US00PP15136P2

(12) United States Plant Patent
Freyre

(10) Patent No.: US PP15,136 P2
(45) Date of Patent: Sep. 7, 2004

(54) ANAGALLIS PLANT NAMED 'WILDCAT ORANGE'

(50) Latin Name: *Anagallis monelli*
Varietal Denomination: Wildcat Orange

(75) Inventor: Rosanna Freyre, Durham, NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 10/721,991

(22) Filed: Nov. 25, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—W C Haas
(74) *Attorney, Agent, or Firm*—C. A. Whealy

(57) ABSTRACT

A new and distinct cultivar of Anagallis plant named 'Wildcat Orange', characterized by its compact and outwardly spreading plant habit; freely branching growth habit; numerous single flowers that are orange in color; and good garden performance.

1 Drawing Sheet

Botanical classification/cultivar designation: *Anagallis monelli* cultivar Wildcat Orange.

BACKGROUND OF THE INVENTION

The present Invention relates to a new and distinct cultivar of Anagallis plant, botanically known as *Anagallis monelli,* and hereinafter referred to by the cultivar name Wildcat Orange.

The new Anagallis is a product of a planned breeding program conducted by the Inventor in Durham, N.H. The objective of the breeding program is to create new compact Anagallis plants with freely and early flowering habit.

The new Anagallis originated from a self-pollination made by the Inventor on Jun. 10, 1999 of a proprietary selection of *Anagallis monelli* identified as code number UNH 13-C8, not patented. The new Anagallis was selected as a single plant from the resulting progeny of the self-pollination in Durham, N.H., on the basis of its plant habit and attractive flower coloration.

Asexual reproduction of the new cultivar by terminal vegetative cuttings since Feb. 15, 2000, taken in Durham, N.H. has shown that the unique features of this new Anagallis are stable and reproduced true to type in successive generations.

SUMMARY OF THE INVENTION

Plants of the cultivar Wildcat Orange have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Wildcat Orange'. These characteristics in combination distinguish 'Wildcat Orange' as a new and distinct cultivar:

1. Compact and outwardly spreading plant habit.
2. Freely branching growth habit:
3. Numerous single flowers that are orange in color.
4. Good garden performance.

In side-by-side comparisons conducted in Durham, N.H., plants of the new Anagallis differed from plants of the parent selection, in the following characteristics:

1. Plants of the new Anagallis had larger flowers than plants of the parent selection.
2. Flowers of plants of the new Anagallis had five petals whereas flowers of plants of the parent selection had four petals.

Plants of the new Anagallis can be compared to plants of the Anagallis cultivar Sunrise, not patented. In side-by-side comparisons conducted in Durham, N.H., plants of the new Anagallis differed from plants of the cultivar Sunrise in the following characteristics:

1. Plants of the new Anagallis were more upright and vigorous than plants of the cultivar Sunrise.
2. Plants of the new Anagallis had longer internodes than plants of the cultivar Sunrise.
3. Plants of the new Anagallis had larger leaves than plants of the cultivar Sunrise.
4. Plants of the new Anagallis had larger flowers than plants of the cultivar Sunrise.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Anagallis.

The photograph at the top of the sheet comprises a side perspective view of three typical plants of 'Wildcat Orange' grown in a container.

The photograph at the bottom of the sheet is a close-up view of typical flowers and leaves of 'Wildcat Orange'.

DETAILED BOTANICAL DESCRIPTION

The aforementioned photographs and following observations and measurements describe plants grown in Bonsall, Calif., in a polyethylene-covered greenhouse during the summer under full sun conditions with day temperatures ranging from about 18 to about 35° C. and night temperatures ranging from about 7 to about 18° C. After planting rooted cuttings, plants were grown for about four months in 20-cm containers with three plants per container. Color references are made to The Royal Horticultural Society Colour Chart, 1995 Edition, except where general terms of ordinary dictionary significance are used.

Botanical classification: *Anagallis monelli* cultivar Wildcat Orange.

Parentage:

*Female parent.*—Proprietary selection of *Anagallis monelli* identified as code number UNH 13-C8, not patented.

*Male parent.*—Proprietary selection of *Anagallis monelli* identified as code number UNH 13-C8, not patented.

Propagation:

*Type cutting.*—Terminal vegetative cuttings.

*Time to initiate roots, summer.*—About five days at 24° C.

*Time to initiate roots, winter.*—About seven days at 24° C.

*Time to develop roots, summer.*—About 20 days at 24° C.

*Time to develop roots, winter.*—About 25 days at 24° C.

*Root description.*—Fine, fibrous; white, close to 155D, in color.

*Rooting habit.*—Freely branching.

Plant description:

*Form.*—Annual flowering plant; compact; initially upright, then semi-upright to outwardly spreading and trailing; uniformly mounded plant form. Freely branching habit with lateral branches potentially forming at very node.

*Plant height.*—About 17 cm.

*Plant diameter* (*area of spread*), *single plant.*—About 30 cm.

*Vigor.*—Vigorous; rapid growth rate.

*Lateral branches.*—Length: About 31 cm. Diameter: About 2.25 mm. Internode length: About 2.5 cm. Texture: Smooth, glabrous. Color: 146C.

*Foliage description.*—Arrangement: Opposite; towards terminals, in whorls of three; simple; sessile. Length: About 1.5 cm. Width: About 5 mm. Shape: Narrowly oblanceolate. Apex: Acute. Base: Truncate. Margin: Entire. Texture, upper and lower surfaces: Glabrous, smooth. Venation pattern: Pinnate, arcuate. Color: Developing leaves, upper and lower surfaces: 147B. Fully expanded leaves, upper surface: 147A. Fully expanded leaves, lower surface: 147B with minute random spots, 185B. Venation, upper surface: 147A. Venation, lower surface: 147B.

Flower description:

*Flower type and habit.*—Single star-shaped flowers; flowers face mostly upward or outward; terminal or axillary; freely flowering habit, about 12 open flowers and about 18 flower buds per lateral branch at one time.

*Natural flowering season.*—Plants flower from April to October in the Northern Hemisphere until frost in the autumn; flowering continuous during this period. Plants start flowering about six to eight weeks after planting rooted cuttings. Flowers not persistent.

*Flower longevity on the plant.*—About four to five days.

*Fragrance.*—None detected.

*Flower size.*—Diameter: About 2 cm. Depth (height): About 8 mm.

*Flower buds.*—Length: About 7 mm. Diameter: About 3 mm. Shape: Ovate. Color: 39B.

*Petals.*—Quantity/arrangement: About five petals arranged in a single whorl. Length: About 1.1 cm. Width: About 8 mm. Shape: Obovate. Apex: Rounded. Base: Attenuate. Margin: Entire. Texture, upper and lower surfaces: Smooth, velvety. Color: When opening, upper surface: 32A. When opening, lower surface: 38A. Fully opened, upper surface: 32B; towards base, 57A. Fully opened, lower surface: 38B; towards the base, 61C.

*Sepals.*—Arrangement/appearance: Five sepals arranged in a single whorl; star-shaped. Length: About 3 mm. Width: About 1 mm. Shape: Elliptical. Apex: Acute. Base: Truncate. Margin: Entire. Texture, upper and lower surfaces: Smooth, glabrous. Color, upper and lower surfaces: 137B.

*Peduncles.*—Length: About 2 cm. Width: Less than 1 mm. Angle: About 80 to 90° from the main stem, then more upright. Strength: Moderately strong. Texture: Smooth, glabrous. Color: 146B.

*Reproductive organs.*—Stamens: Quantity per flower: About five. Anther shape: Curved; sickle-shaped. Anther length: About 2 mm. Anther width: About 1 mm. Anther color: 13A. Pollen amount: Scarce. Pollen color: 13A. Pistils: Quantity per flower: One. Pistil length: About 6 mm. Style length: About 3 mm. Style color: 54B. Stigma shape: Rounded. Stigma color: 151B. Ovary color: 145B.

*Seed/fruit.*—Seed and/or fruit production has not been observed.

Disease/pest resistance: Plants of the new Anagallis have not been noted to be resistant to pathogens or pests common to Anagallis.

Garden performance: Plants of the new Anagallis have been observed to have good garden performance. Plants of the new Anagallis have been noted to tolerate temperatures from below 0 to 40° C. and have excellent tolerance to rain and wind.

It is claimed:

1. A new and distinct cultivar of Anagallis plant named 'Wildcat Orange', as illustrated and described.

* * * * *

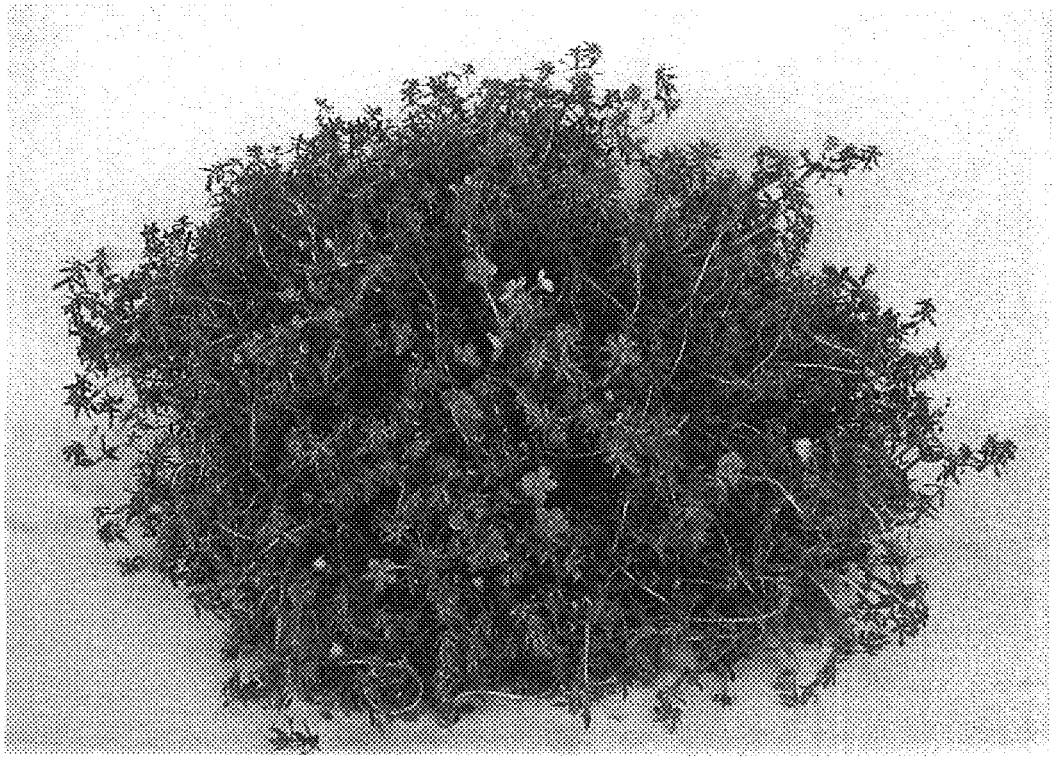
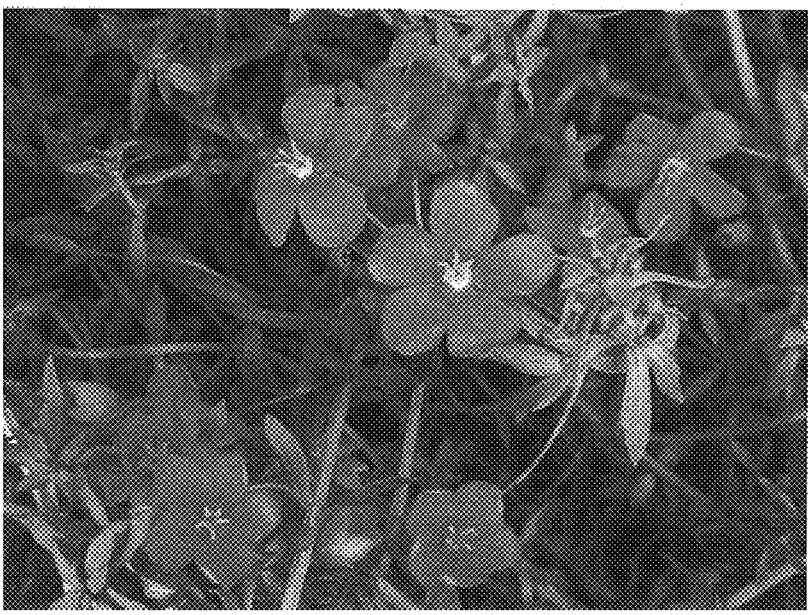

UNITED STATES PATENT AND TRADEMARK OFFICE

CERTIFICATE OF CORRECTION

PATENT NO. : PP 15,136 P2
DATED : September 7, 2004
INVENTOR(S) : Rosanna Freyre It is certified that error appears in the above-identified patent and that said Letters Patent is hereby corrected as shown below:

Column 1,
Line 1, the following statement of federal sponsorship should be added,
-- This invention was made with government support under USDA/CSREES Cooperative Agreement Number 01-90015-0420 awarded by the US Department of Agriculture Cooperative State Research, Education, and Extension Service. The government has certain rights in the invention. --

Signed and Sealed this

Twenty-sixth Day of April, 2005

JON W. DUDAS
*Director of the United States Patent and Trademark Office*